United States Patent [19]

Lindell et al.

[11] 4,218,299
[45] Aug. 19, 1980

[54] SHORT PATH LIQUID JUNCTION STRUCTURE FOR ELECTROCHEMICAL ELECTRODES

[75] Inventors: Grover F. Lindell; George Matsuyama, both of Santa Ana, Calif.

[73] Assignee: Beckman Instruments, Inc., Fullerton, Calif.

[21] Appl. No.: 55,252

[22] Filed: Jul. 6, 1979

[51] Int. Cl.² ................ G01N 27/30; G01N 27/36
[52] U.S. Cl. ........................... 204/195 F; 204/195 G
[58] Field of Search ............... 204/195 F, 195 G; 128/635; 324/438

[56] References Cited

U.S. PATENT DOCUMENTS

| | | | |
|---|---|---|---|
| 3,264,205 | 8/1966 | Leonard et al. | 204/195 F |
| 3,741,884 | 6/1973 | DeUshane et al. | 204/195 F |
| 4,105,509 | 8/1978 | Jungck | 204/195 F X |
| 4,128,468 | 12/1978 | Bukamier | 204/195 F |

*Primary Examiner*—G. L. Kaplan
*Attorney, Agent, or Firm*—Robert J. Steinmeyer; Robert R. Meads; John R. Shewmaker

[57] ABSTRACT

A short path liquid junction structure is defined through a porous ceramic layer coated circumferentially on an electrochemical electrode glass body by an elastomeric O-ring sealing member circumferentially engaging the ceramic layer in an annular line contact seal. The length of the liquid junction path is the short distance through the porous ceramic layer around and past the line contact seal.

4 Claims, 4 Drawing Figures

SHORT PATH LIQUID JUNCTION STRUCTURE FOR ELECTROCHEMICAL ELECTRODES

BACKGROUND OF THE INVENTION

1. Field of the Invention

The present invention relates generally to liquid junction structures for electrochemical electrodes and, more particularly, to liquid junction structures particularly adapted for glass electrode bodies.

2. Description of the Prior Art

In general liquid junction structures are incorporated in electrochemical electrodes which measure ions in solution in order to establish electrolytic contact between the solution to be tested and an electrolyte within the electrode. The liquid junction structure should establish electrolytic contact between the two solutions without introducing an extraneous electrical potential generally referred to as a liquid junction potential for a reference electrode. With an ideal liquid junction the potential of a reference electrode remains constant and is substantially independent of the solution being tested. The ideal characteristics of a liquid junction are well defined in the art. Though numerous liquid junction structures have been developed, refined, discarded and rediscovered, and such over the years, the search continues for further structures approaching the elusive ideal characteristics.

Among the ideal characteristics, a liquid junction structure should establish electrolytic contact by diffusion or, if by flow, then at a very even, continuous, low flow rate. The liquid junction should have a low or negligible impedance, should resist clogging, should be easily wet despite its low flow rate, and should be easily cleanable. In addition, the junction should not generate potentials dependent upon the sample composition.

U.S. Pat. No. 3,264,205 discloses a liquid junction structure comprising a porous ceramic coating which is particularly adapted for glass electrode bodies. The ceramic coating is readily fired onto the glass body. In one embodiment the patent discloses an outer tubular glass body having such ceramic coated around the inner surface of one open end. The open end is closed by a rubber stopper and the liquid junction path is defined through the porous ceramic coating along the length of the rubber stopper to the electrolyte reservoir inside the glass body. An inner glass pH measuring electrode extends through the stopper coaxially within the outer glass body, and the patent teaches that the ceramic could in theory be coated around the outer surface of the glass pH electrode to establish an alternative liquid junction path through the ceramic along the pH electrode for the full length of the rubber stopper. Where a flowing liquid junction structure is employed, i.e. where a slight head pressure induces liquid flow through the junction, the relatively long length of the foregoing porous ceramic junction is not a serious advantage. However, where an ionic diffusion junction, as opposed to a flowing junction, is desired the long junction path is a definite disadvantage. Diffusion junctions are employed in non-refillable type electrodes where depletion of electrolyte is to be avoided. Such non-refillable electrodes are sealed at manufacture and are discarded when the electrolyte is depleted. In a diffusion junction there is no flow and the diffusion of ions through the solution takes place at an extremely slow rate. Consequently, use of such an electrode in different solutions will allow various sample solutions to leach out the ions of the reservoir electrolyte from the junction and replace them with sample solution components.

The ions of the reservoir electrolyte are specially chosen so that the cations have the same mobility as the anions. These ions are also present at relatively high concentrations in the reservoir electrolyte so any contamination by samples will have a minimal effect on the mobilities of cations and anions. This arrangement minimizes liquid junction potentials at the reference electrode. With a flowing junction the reservoir electrolyte is constantly flowing through the liquid junction. This prevents the ingress of sample components and keeps the junction filled with reservoir electrolyte. With a diffusion junction, on the other hand, when it is immersed in different solutions the ions of the reservoir electrolyte can diffuse into the sample solution and be replaced by components of the sample. Since these ions will probably not have equal mobility of cations and anions, a liquid junction potential can arise. This effect can be counteracted by diffusion of ions from the reservoir into the liquid junction since the concentration of reservoir electrolyte is relatively high. Since the diffusion process is very slow the replenishing of electrolyte in the liquid junction cannot take place if the junction is thick or long.

SUMMARY OF THE INVENTION

The present invention resides in a liquid junction structure which overcomes the disadvantages of long or thick flow path junctions by establishing a short junction path for glass electrode bodies which is particularly advantageous for diffusion-type liquid junctions. To these ends the invention in its broadest aspects contemplates an electrochemical electrode assembly including a nonconductive container having an opening receiving and surrounding an inner glass body, a coating of porous ceramic bonded to an outer circumferential surface of the glass body and extending axially thereon to provide a liquid junction path through the ceramic, and an improved arrangement including an annular sealing member surrounding the glass body and porous coating for closing the container opening and defining a short path junction. The sealing member includes a sealing surface circumferentially engaging and sealing against the porous ceramic coating and the sealing surface is arcuately configured in axial section along the glass body. In this manner the sealing surface establishes a generally annular line contact seal with the porous ceramic coating whereby a short path liquid junction is defined in the axial direction exclusively through the ceramic coating for the relatively short distance traversing the annular line contact seal. In the preferred embodiments the sealing member is an elastomeric O-ring.

Short path junctions of the foregoing nature are suitable for the reference portion of a combination electrode or for a reference electrode itself. For a combination electrode the glass body defines a measuring electrode received within a non-conductive container of plastic or glass. When the container is also glass, its inner circumferential surface may similarly be coated with a porous ceramic in which case either or both inner and outer circumferential sealing surfaces of the annular member establish short path junctions through the ceramic coatings of the container and of the tubular glass body. For a reference electrode the inner glass body can be configured as a tubular or a solid rod on which the ceramic is deposited.

DESCRIPTION OF THE PREFERRED EMBODIMENTS

Figure 3:
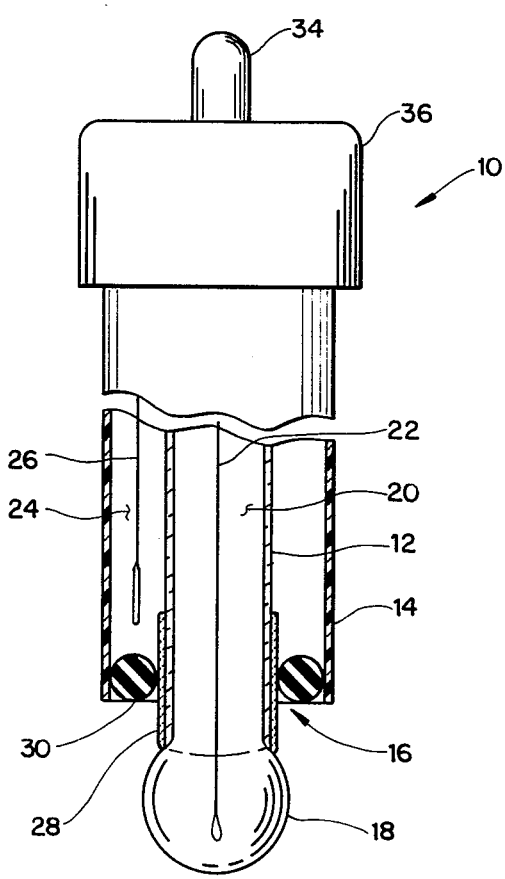
FIG. 3 illustrates the tubular body of FIG. 2 as incorporated in a combination electrode assembly having a liquid junction structure of the present invention.

As shown in the drawing for purposes of illustration, and particularly FIG. 3 thereof, the invention is there embodied in an electrochemical combination electrode, indicated generally by numeral 10, which comprises a measuring electrode glass body 12 supported near its opposite ends to extend coaxially within a generally tubular hollow container 14, and a novel liquid junction structure, indicated generally by numeral 16, in accordance with the present invention at the lower end of the electrode. Measuring electrode 12 is illustrated as a conventional tubular glass pH electrode with a pH sensitive glass bulb 18 blown on its lower end. The interior of tubular body 12 is filled with an internal electrolyte 20 such as saturated potassium chloride solution in which an indicating silver-silver chloride half cell 22 conductor is immersed. The combination electrode could include as measuring electrode 12 any other conventional ion-measuring electrode structures for measuring any desired ion of interest such as the platinum electrode described in our copending application Ser. No. 055,253 filed concurrently herewith.

Tubular container 14 in the FIG. 3 embodiment is formed of nonconductive material such as a polypropylene or other plastic but could alternatively be formed of glass. The annular space between tubes 12 and 14 defines a reservoir receiving a reference electrolyte 24 such as a saturated potassium chloride solution in which a reference silver-silver chloride half cell 26 is immersed. Liquid junction structure 16 of the invention establishes ionic contact between the reference electrolyte 24 and a solution to be tested.

Figure 1:
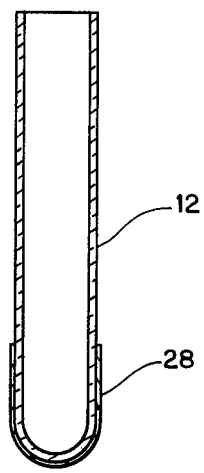
FIG. 1 is a cross-sectional view taken in a generally vertical plane through a tubular glass body, closed at one end, and having a ceramic layer bonded to the closed end.
Figure 2:
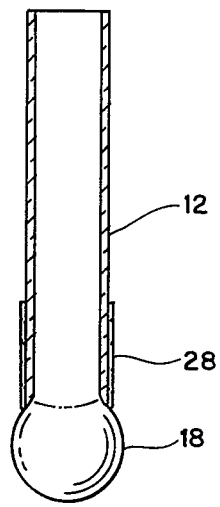
FIG. 2 illustrates a glass tubular body similar to that of FIG. 1 having the end ground off and a pH glass bulb blown on the tube end.

The liquid junction structure 16 comprises a layer 28 of porous ceramic which coats the circumference of glass tube 12 above glass bulb 18 and is encircled by an annular sealing member 30 which closes the lower end of container 14 and cooperates to define a short liquid junction path for the electrode. In fabrication of the electrode assembly, referring to FIG. 1, a glass tube 12 closed at its bottom end is dipped into a thick slurry of clay-like material known as a ceramic slip to form the layer of porous ceramic coating 28 thereon. Reference is made to aforementioned U.S. Pat. No. 3,264,205 teaching the coating of glass electrode bodies with such material. As noted therein, any number of such slurries are known and may be used for the purposes of the present invention. An illustrative example of such composition comprises 50% California talc by weight dry, 16% Kentucky No. 4 ball clay, 16% plastic vitrox (Flint-Feldspar), 16% Tennessee No. 1 ball clay, and 2% Kentucky special ball clay. This composition is mixed with water to form the slip and the tube dipped into it. The tube is withdrawn and allowed to drain and dry. If desired, the tube may be dipped several times in order to obtain the desired thickness. Between each dipping, however, the dipped surface must be sufficiently dry so that the new coating will adhere.

After a coating of desired thickness of the ceramic material is attained, the coating is thoroughly dried and then fused. Fusion is performed by applying heat using an oven or an open torch or other suitable means. The coating must be heated to a temperature sufficient to partially fuse the ceramic mass but not sufficient to cause it to run and totally fuse. An over-fired coating will become impervious to water penetration and thus be useless as a liquid junction. Although the temperature range for proper fusion varies from material to material, generally speaking the ceramic mass should be heated to a temperature of approximately 820° C. when the tubing to be coated is Corning Pyrex glass or to a somewhat lower value of about 650+ C. when lead glass is used. The teachings of the aforementioned patent are specifically incorporated herein by reference.

After ceramic coating 28 is fused to the tube, the bottom end of the tube is ground off and pH sensitive glass bulb 18 is blown thereon in a conventional manner. Tube 12 is then ready for insertion into the lower open end of container 14 to the position illustrated in FIG. 3.

At the upper end of the electrode a connecting coaxial cable 34 is connected to half cell electrodes 22 and 26 and the electrode is closed by a cap 36 all in a conventional manner.

In accordance with a primary aspect of the present invention, annular sealing member 30 closes and seals the lower opened end of container 14 and coacts with ceramic coating 28 on glass body 12 to define a short liquid junction path through the ceramic between reference electrolyte 24 and the solution to be tested. To this end the sealing member comprises an elastomeric O-ring which, in vertical cross-section (FIG. 3), is circular. With such circular cross section, the sealing O-ring has (1) an inner annular sealing surface which surrounds and seals against ceramic layer 28 and which is curved or arcuate in configuration in the axial direction along the electrode assembly and (2) an outer annular sealing surface which circumferentially engages the inner surface of container 14 and which also is curved or arcuate in configuration. The ceramic layer, in vertical cross-section (FIG. 3), is linear. Significantly, the inner sealing surface of the sealing ring circumferentially surrounds engages and seals against ceramic layer 28 to define an annular line contact seal circumferentially around the ceramic coating. As a result, the liquid junction path through the ceramic is simply that short path therethrough around the line contact seal. The short junction path is ideally suited for defining an ion diffusion path for an electrode 10 of a non-refillable type having the electrolyte 24 permanently sealed therein. Silicone rubber, neoprene, or any material exhibiting similar characteristics are suitable for forming O-ring 30.

Figure 4:
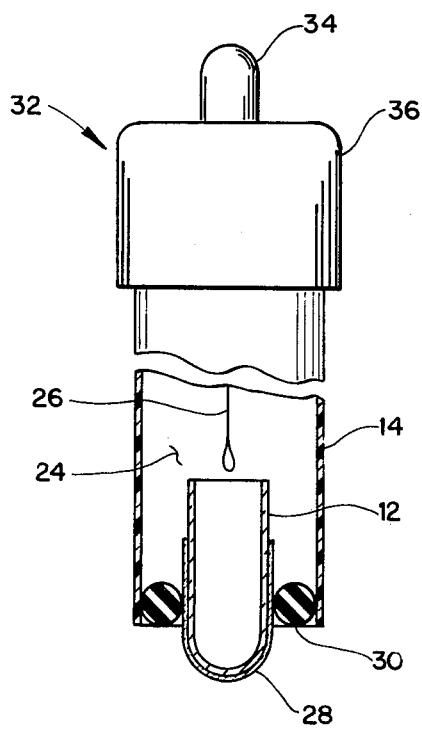
FIG. 4 illustrates a reference electrode in accordance with the present invention.

FIG. 4 illustrates the liquid junction structure incorporated in a reference electrode 32, indicated generally by numeral 32, whose elements are numbered similarly to the combination electrode of FIG. 3. In the reference electrode the inner ion measuring portion is eliminated and the tubular glass structure of FIG. 1, shortened by cutting off its top, is received in the open end of container 14. Ceramic layer 28 coats the closed lower end of tube 12. Annular sealing member 30, identical to that of FIG. 3, circumferentially engages and seals the circumference of the ceramic layer to define a short junction path through the ceramic. The electrode structure may be simplified by replacing glass tubular body 12 with a solid glass rod or stem coated circumferentially with ceramic layer 28.

It will be understood that for both the combination electrode of FIG. 3 and the reference electrode of FIG. 4, when tubular container 14 is formed of glass, then the inner annular surface of the container may be coated with the ceramic 28. In such case the outer circumferential surface of sealing member 30 would engage and seal against this inwardly facing ceramic layer to define a liquid junction path therethrough. In such a structure the ceramic layer bonded to container 14 could either replace the ceramic layer on body 12 in which case the inner sealing surface of member 30 would seal directly against body 12, or it could supplement the ceramic coating on body 12 in which case parallel short liquid junction paths would be formed through the respective ceramic layers coated on tube 12 and on container 14.

It will be apparent from the foregoing that applicants have devised a useful and novel short path liquid junction structure for ceramic coated glass electrode bodies. The junction is ideally suited for establishing ion diffusion-type junctions for use either in reference or combination electrodes and particularly such electrodes of the non-refillable type. For either case it minimizes liquid junction potentials at the reference junction by minimizing the distance which must be traversed through the junction by slowly moving ions in solution. Moreover, while several preferred embodiments of the invention have been illustrated and described, it will be apparent that various modifications may be made therein without departing from the spirit and scope of the invention as defined in the following claims.

What is claimed is:

1. In an electrochemical electrode assembly including a nonconductive container having an opening receiving and surrounding a tubular or solid glass body, a coating of porous ceramic bonded to an outer circumferential surface of the glass body and extending axially thereon to provide a liquid junction path through which electrolytic communication is established between an electrolyte within the electrode assembly and a solution to be tested, an improved arrangement for closing the container opening comprising:

an annular sealing member having a sealing surface circumferentially engaging and sealing against the porous ceramic coating, the sealing surface being of arcuate configuration in axial cross-section to establish a generally annular line contact seal around the circumferential surface of the porous ceramic coating whereby a short path liquid junction is defined in the axial direction exclusively through the porous ceramic coating for the relatively short distance traversing the annular line contact seal.

2. In an electrochemical electrode assembly including a first glass tubular body having an open end generally coaxially receiving and surrounding a second glass tubular or solid body, a coating of porous ceramic bonded to one or both of (1) the outer annular surface of the second glass body, and (2) the inner annular surface of the first glass body and extending axially therealong to provide a liquid junction structure establishing electrolytic communication between an electrolyte within the electrode assembly and a solution to be tested, an improved arrangement surrounding the second glass body for closing the container opening comprising:

an annular sealing member having inner and outer annular sealing surfaces one or each of which circumferentially engage and seal against a respective coating of porous ceramic, each sealing surface(s) so engaged being of arcuate configuration in axial cross-section to establish a generally annular line contact seal with the circumferential surface of the porous ceramic coating(s) whereby a short path liquid junction is defined in the axial direction exclusively through the porous ceramic coating(s) for the relatively short distance traversing the annular line contact seal.

3. The electrode assembly of claim 1 or claim 2 wherein the annular sealing member is an O-ring of elastomeric material.

4. The electrode assembly of claim 3 wherein the O-ring elastomeric material comprises silicone rubber or neoprene.

* * * * *